US009669123B2

(12) United States Patent
Levsen et al.

(10) Patent No.: US 9,669,123 B2
(45) Date of Patent: Jun. 6, 2017

(54) DEODORIZING AND SANITIZING CONTAINER

(71) Applicant: Hantover, Inc., Overland Park, KS (US)

(72) Inventors: Clark A. Levsen, Shawnee, KS (US); Hilary Lynne Huff Philgreen, Leawood, KS (US)

(73) Assignee: Hantover, Inc., Overland Park, KS (US)

( * ) Notice: Subject to any disclaimer, the term of this patent is extended or adjusted under 35 U.S.C. 154(b) by 168 days.

(21) Appl. No.: 14/055,766

(22) Filed: Oct. 16, 2013

(65) Prior Publication Data

US 2014/0105783 A1    Apr. 17, 2014

Related U.S. Application Data

(60) Provisional application No. 61/715,132, filed on Oct. 17, 2012.

(51) Int. Cl.
*A61L 9/00* (2006.01)
*A61L 2/20* (2006.01)
*A47L 23/20* (2006.01)

(52) U.S. Cl.
CPC ............. *A61L 2/202* (2013.01); *A47L 23/205* (2013.01); *A61L 2209/212* (2013.01)

(58) Field of Classification Search
CPC ... A61L 2/202; A61L 2202/26; A61L 2202/15
USPC .................................................. 422/186.05
See application file for complete search history.

(56) References Cited

U.S. PATENT DOCUMENTS

| 2,201,548 | A |   | 5/1940 | Treinis |
| 2,350,091 | A |   | 5/1944 | Bergman |
| 3,078,526 | A | * | 2/1963 | Caruso .................... A61L 2/202 |
|           |   |   |        | 194/242 |
| 3,793,744 | A | * | 2/1974 | Saita .................... A43D 3/1491 |
|           |   |   |        | 34/104 |
| 5,978,996 | A |   | 11/1999 | Ullman |

(Continued)

FOREIGN PATENT DOCUMENTS

| CN | 2597511 | 1/2004 |
| CN | 201175464 | 1/2009 |

(Continued)

OTHER PUBLICATIONS

International Search Report and Written Opinion from PCT Application No. PCT/US2013/065446 entitled Deodorizing and Sanitizing Container (Dated Feb. 20, 2013).

(Continued)

*Primary Examiner* — Kevin Joyner
(74) *Attorney, Agent, or Firm* — Hovey Williams LLP

(57) ABSTRACT

Improved, portable apparatus for ozone deodorizing and sanitizing of clothing items such as shoes is provided having a housing sized to receive an item to be treated, together with an ozone generator and a ventilation assembly operable to deliver ozone-laden air currents into the housing. In preferred forms, the ozone generator is located within a compartment separate from the housing, and a fan assembly is used to draw ambient air currents adjacent the generator for ozone supplementation, followed by delivery of the ozone-laden air currents into the housing.

26 Claims, 6 Drawing Sheets

(56) References Cited

U.S. PATENT DOCUMENTS

| | | | |
|---|---|---|---|
| 6,134,806 | A | 10/2000 | Dhaemers |
| 6,585,935 | B1 | 7/2003 | Taylor et al. |
| 6,872,366 | B2 | 3/2005 | Thomas et al. |
| 7,121,421 | B2 | 10/2006 | Yang et al. |
| 7,922,024 | B2 | 4/2011 | Yang et al. |
| 7,960,706 | B2 | 6/2011 | Ullman |
| 2001/0010806 | A1 | 8/2001 | Kanazawa et al. |
| 2005/0204579 | A1* | 9/2005 | Rosseau .................. A47L 23/20 34/104 |
| 2007/0086914 | A1* | 4/2007 | Antinozzi ................. A61L 2/18 422/28 |
| 2008/0118411 | A1 | 5/2008 | D'Arinzo |
| 2010/0040515 | A1 | 2/2010 | Lovelace |
| 2011/0048474 | A1 | 3/2011 | Kim |
| 2011/0194981 | A1 | 8/2011 | Chen et al. |
| 2011/0240883 | A1 | 10/2011 | Ullman |
| 2015/0008336 | A1 | 1/2015 | Rubinchikov et al. |

FOREIGN PATENT DOCUMENTS

| | | |
|---|---|---|
| CN | 201524055 | 7/2010 |
| JP | H10137007 | 5/1998 |
| RU | 109968 U1 | 11/2011 |

OTHER PUBLICATIONS

Office Action from Serial No. CN 201380054045.0 (dated Oct. 10, 2016) (English translation attached).

* cited by examiner

DEODORIZING AND SANITIZING CONTAINER

CROSS-RELATED APPLICATIONS

This application claims the benefit of Provisional Patent Application Ser. No. 61/715,132 filed Oct. 17, 2012, which is hereby incorporated by reference herein in its entirety.

BACKGROUND OF THE INVENTION

Field of the Invention

The present invention is broadly concerned with a deodorizing and sanitizing apparatus using ozone-laden air currents. More particularly, the invention is concerned with such apparatus, and corresponding methods, wherein ambient air is drawn into proximity with an ozone generator for creating the ozone-laden air currents prior to passage thereof into a housing adapted to hold a item of clothing (e.g., shoes) to be treated.

Description of the Prior Art

Ozone is a triatomic form of oxygen (O3), and is known to be the strongest oxidant of common disinfecting agents. Ozone has been used at least since 1893 for treatment of drinking water, and today is the most commonly used disinfection process in Europe. A wide spectrum of organisms is destroyed by ozone, and the ability of ozone to remove taste and odors is excellent. Generally, ozone is used in the same manner as chlorine, but it does not present many of the handling problems of chlorine. However, ozone is unstable so it cannot effectively be produced and transported to the point of use. Rather, it must be generated at or close to the point of use. Ozone may be generated using known equipment, especially corona discharge tubes and UV radiation devices.

Ozone generators have been used by dry cleaning establishments in order to clean and restore clothing and fabrics harmed by fire and smoke. These generators are designed to be placed within a room and include a small fan for circulating ozone-supplemented air. Generally, these units must be operated for hours or even days to be effective, and such are not suitable for use in homes.

SUMMARY OF THE INVENTION

The present invention provides improved apparatus and methods for treating clothing items using ozone. Broadly speaking, the invention includes structure defining an enclosed treatment zone operable to hold an item of clothing for treatment, an ozone generator, and a ventilation assembly operable to create currents of air containing ozone from the generator, and to pass such ozone-laden air currents in proximity to the item for a period of time sufficient to deodorize and sanitize the item.

According to one aspect of the present invention, a deodorizing and sanitizing apparatus includes structure defining an enclosed treatment zone operable to hold an item of clothing for treatment, an ozone generator, and a ventilation assembly. The ventilation assembly is operable to create currents of air containing ozone from the generator, and to pass such ozone-laden air currents in proximity to the item for a period of time sufficient to deodorize and sanitize the item.

In preferred forms, the zone-defining structure comprises an upright housing having an openable cover allowing access to the interior of the housing, and the ventilation assembly comprises a fan operable to induce ambient air currents past the generator in order to create the ozone-laden air currents, where the ozone generator is located proximal to the fan. Advantageously, the fan and ozone generator are located within a compartment separate from the treatment zone, and a passageway is provided for delivery of the ozone-laden air from the compartment and into the treatment zone. In order to most effectively and efficiently create the ozone-laden currents, it is preferred that the ozone generator be located outside of the treatment zone. Optionally, a heater may be provided for heating the air currents before or after the ozone supplementation thereof. It has also been found to be helpful to have a vent opening in the housing, which is correlated with the ventilation assembly so as to create positive pressure conditions within the zone during treating operations.

According to another aspect of the present invention, an apparatus is provided for deodorizing and sanitizing shoes. The apparatus comprises a base including a bottom wall and an upstanding side wall, with a housing defining a shoe treatment zone secured to the base and extending upwardly therefrom, the housing having a lower wall, upright outer walls, and an openable cover. A pair of upright shoe trees are located within the housing and secured to the housing lower wall. Each tree extends upwardly from the lower wall and comprises a tubular, imperforate shank and a perforate ozone-delivery head extending laterally from the shank The shoe trees are thus operable to support a pair of shoes to be treated, with the tree heads being configured for placement within the confines of the shoes. An ozone generator is positioned within the base and below the housing lower wall. The shoe treatment apparatus further has a ventilation assembly operable to create currents of air containing ozone from the generator, and to pass such ozone-laden air currents through the shoe tree shanks and the heads in order to deodorize and sanitize the shoes. The ventilation assembly includes a fan and a conduit operably coupled with each of the shanks and communicating the interiors of the shanks with the fan.

In preferred forms, the ozone generator and fans located within a segregated compartment of the base. If desired, the apparatus includes a pair of conduits, each associated with a respective one of the trees, and a heater within each of the air conduits for heating of the air currents.

Yet another aspect of the present invention concerns a method of treating clothing items such as shoes. These methods involve the steps of locating the item to be treated within an enclosed treatment zone, and passing ozone-laden air currents into the treatment zone for a time sufficient to deodorize and sanitize the item; the ozone-laden air currents are generated by passing ambient-derived air currents into proximity with an ozone generator.

Preferably, the method involves operating a fan to draw the ambient air currents into the zone after the ambient air currents are supplemented with ozone, particularly where the ozone generator is located within a compartment separate from the treatment zone. If desired, the air currents may be heated prior to passage thereof into the zone. Where shoes are being treated, it is preferred that the ozone-laden air currents be directed into the interiors of the shoes.

This summary is provided to introduce a selection of concepts in a simplified form. These concepts are further described below in the detailed description of the preferred embodiments. This summary is not intended to identify key features or essential features of the claimed subject matter, nor is it intended to be used to limit the scope of the claimed subject matter.

Various other aspects and advantages of the present invention will be apparent from the following detailed description of the preferred embodiments and the accompanying drawing figures.

BRIEF DESCRIPTION OF THE DRAWINGS

Preferred embodiments of the present invention are described in detail below with reference to the attached drawing figures, wherein.

Figure 1:
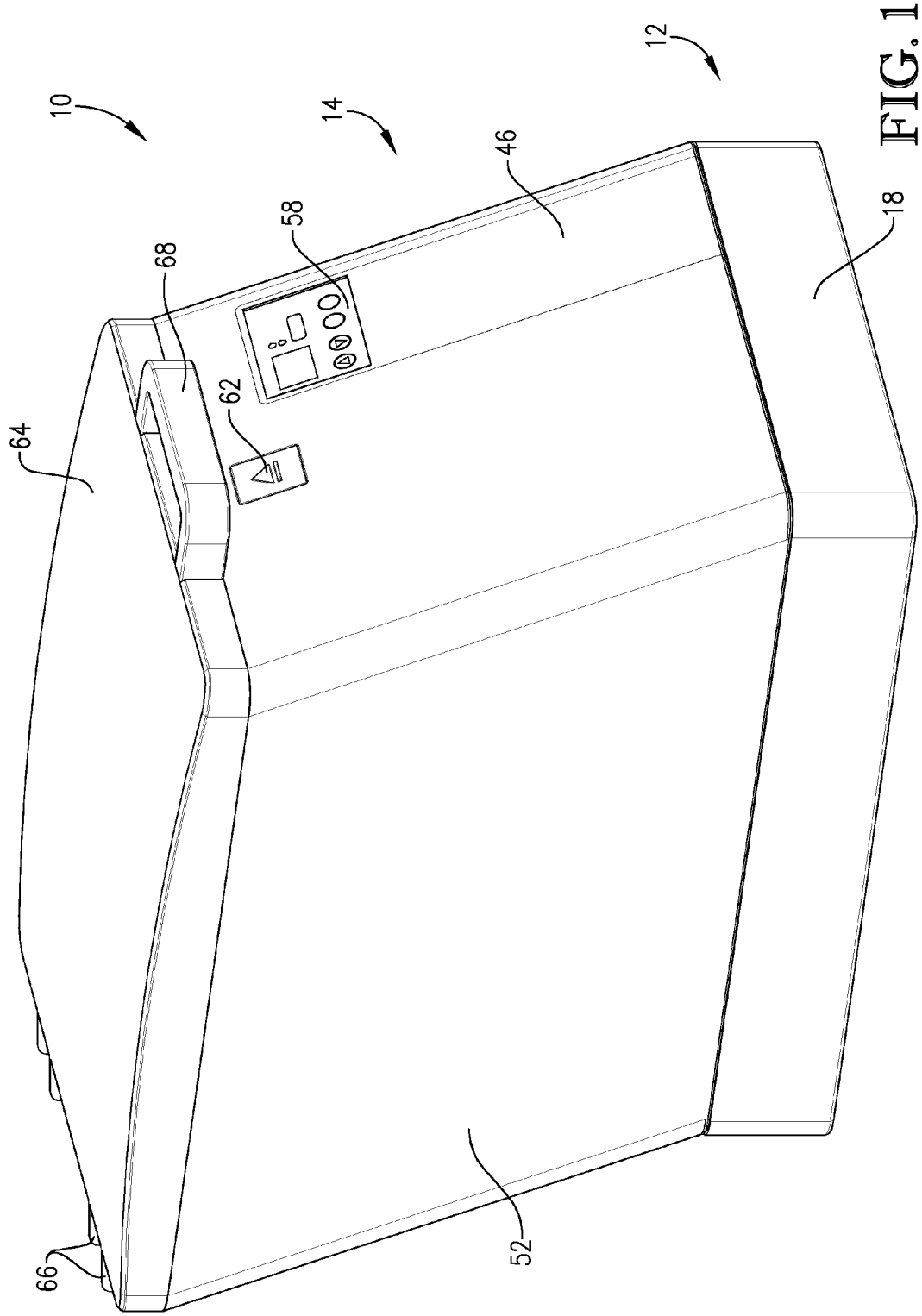
FIG. 1 is a perspective view of the deodorizing and sanitizing apparatus of the invention.

The drawing figures do not limit the present invention to the specific embodiments disclosed and described herein. The drawings are not necessarily to scale, emphasis instead being placed upon clearly illustrating the principles of the preferred embodiments.

DETAILED DESCRIPTION OF THE PREFERRED EMBODIMENT

The present invention is susceptible of embodiment in many different forms. While the drawings illustrate, and the specification describes, certain preferred embodiments of the invention, it is to be understood that such disclosure is by way of example only. There is no intent to limit the principles of the present invention to the particular disclosed embodiments.

Figure 2:
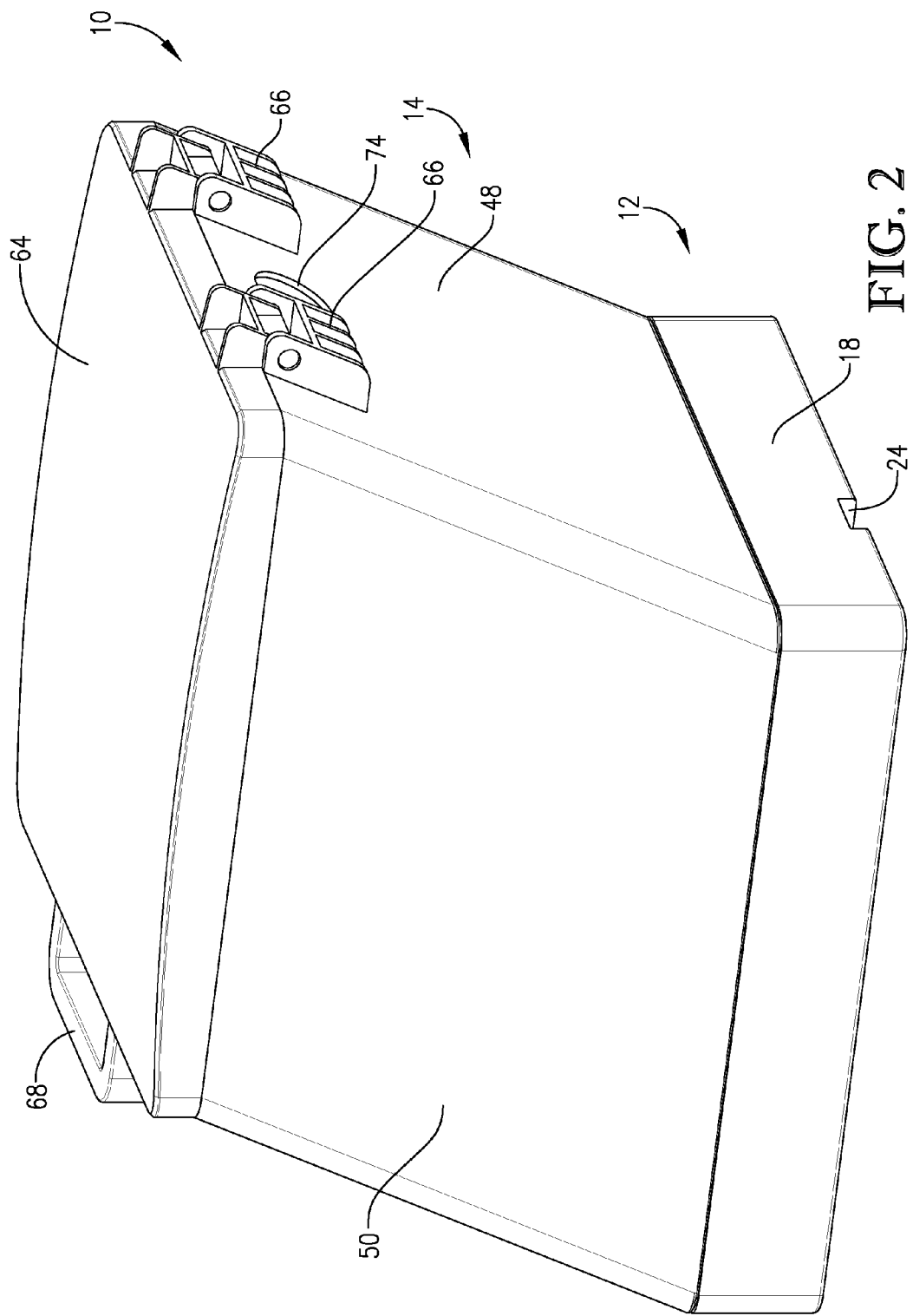
FIG. 2 is another perspective view of the apparatus, illustrating the opposite side of the apparatus as compared with FIG. 1.

Turning now to the drawings, and particularly FIGS. 1-2, a deodorizing and sanitizing apparatus 10 is illustrated. The apparatus 10 broadly includes a base 12 and an upstanding container or housing 14 supported on the base 12. The container 14 is adapted to receive items to be deodorized and sanitized, as will be explained.

Figure 6:
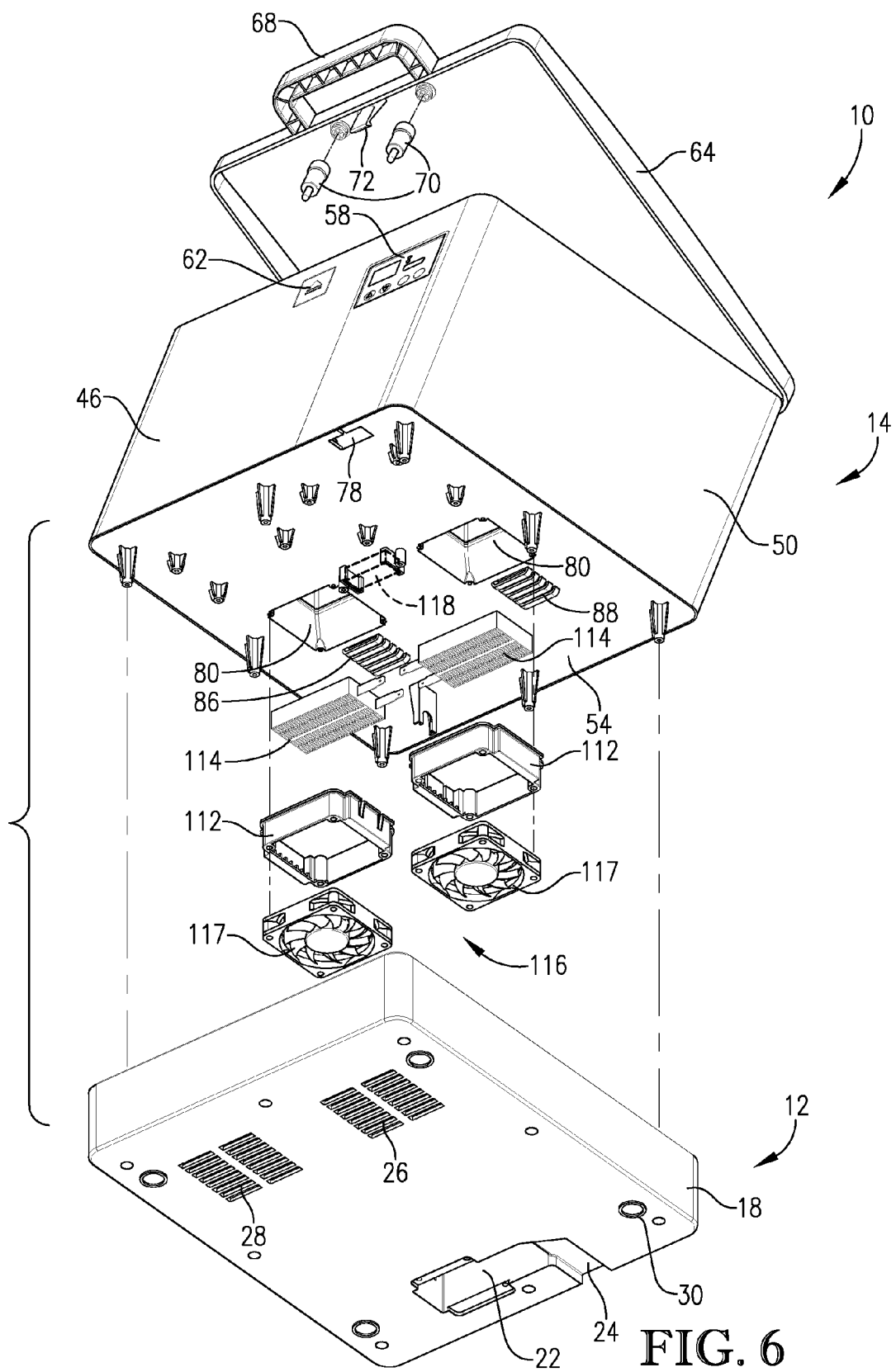
FIG. 6 is another exploded view of the apparatus.

The base 12 includes a bottom wall 16 and a continuous, upwardly extending sidewall 18, with a series of internal, upstanding, integral gussets 20 providing additional support for the sidewall 18. The bottom wall 16 is equipped with an upstanding transformer housing 22 and a recessed passageway 24 extending from sidewall 18 and communicating with the interior of transformer housing 22. The housing 22 holds a conventional electric transformer (not shown), whereas the passageway 24 serves as a wireway for a standard electric cord (also not shown). The bottom wall 16 is also equipped with two sets of vent openings 26 and 28, and corner-mounted feet 30 (FIG. 6).

Internally, the base 12 has a series of upstanding, tubular coupling fixtures 32 and two sets of elongated connector bar members 34 and 36, which are astride the vent openings 26 and 28 and are designed to support electronic control boards (not shown). Finally, an internal, substantially rectangular compartment 38 is provided within base 12, defined by a pair of sidewalls 40 and end walls 42. It will be observed that one of the sidewalls 40 is relieved as at 44 to provide an airway into the confines of compartment 38.

The housing 14 is designed to be mounted on base 12 and broadly includes obliquely oriented front and rear walls 46 and 48, upstanding sidewalls 50, 52 and a lower wall 54, thereby defining a deodorizing and sanitizing zone 56. The front wall 46 supports a controller 58 (including a visible control panel), as well as a latching mechanism 60. The latching mechanism includes an operating button 62. An upright, internal channel housing 63 is provided for the wiring associated with controller 58. An uppermost lid or cover 64 is secured to rear wall 48 by means of hinges 66, and has a forward handle 68 as well as a pair of forward, spaced apart, spring-loaded couplers 70 and a latching tongue 72, the latter being designed to mate with mechanism 60 when the lid 64 is closed. Rear wall 48 has an aperture 74 between the hinges 66, which is important for purposes to be described.

Figure 3:
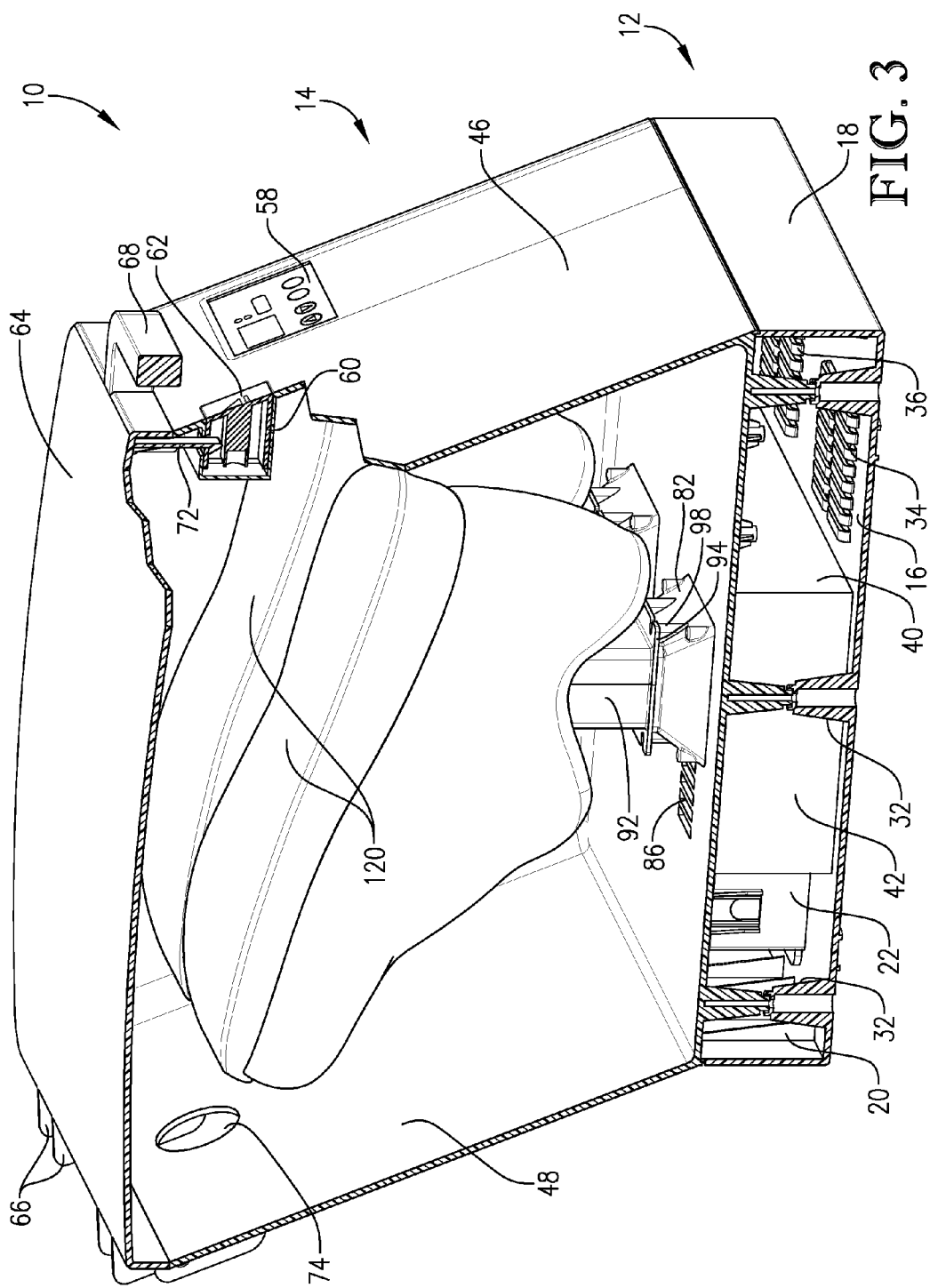
FIG. 3 is a sectional view with parts broken away of the apparatus, shown with a pair of athletic shoes being treated therein.
Figure 4:
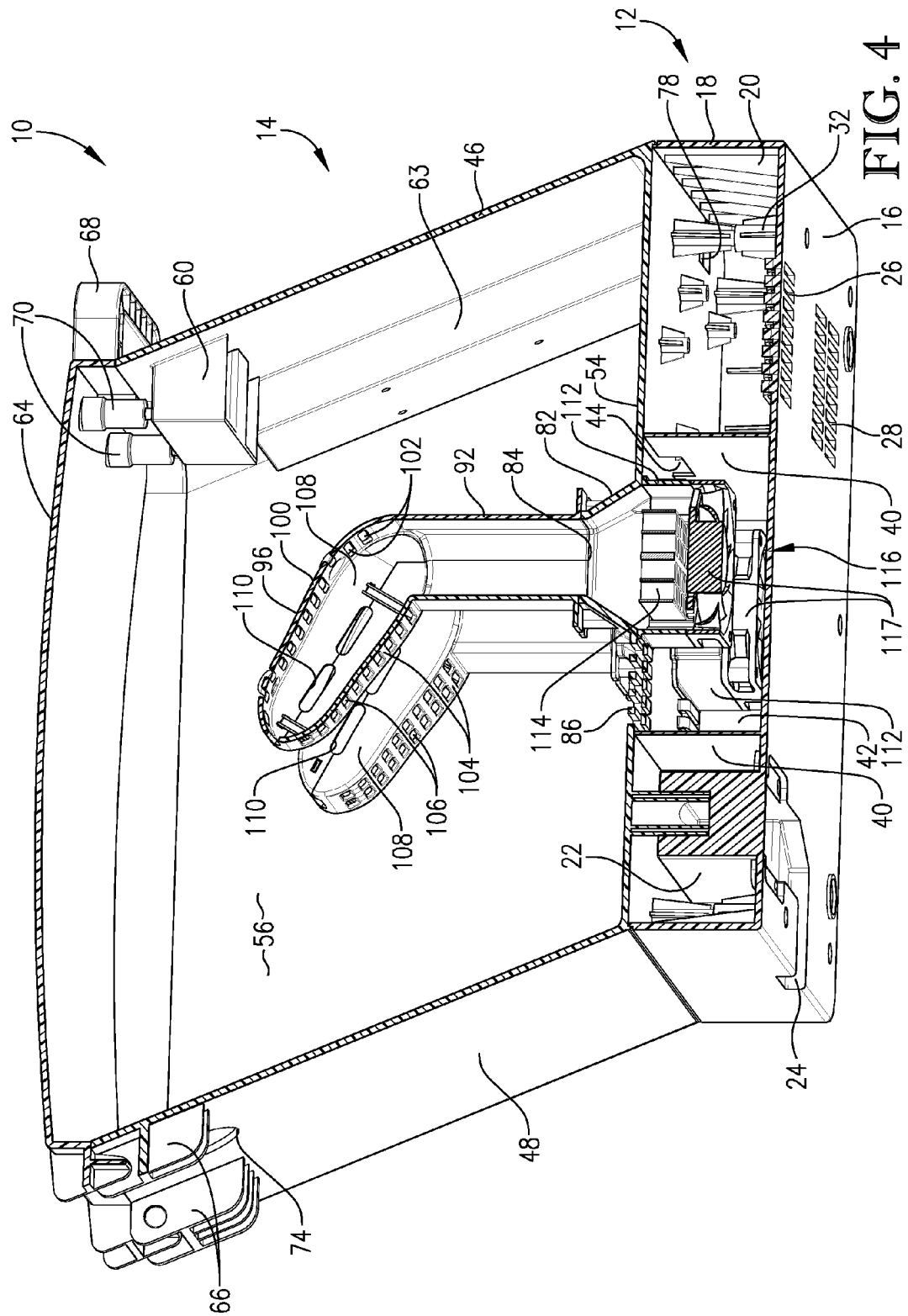
FIG. 4 is a sectional view illustrating the internal construction of the apparatus including the shoe supports.
Figure 5:
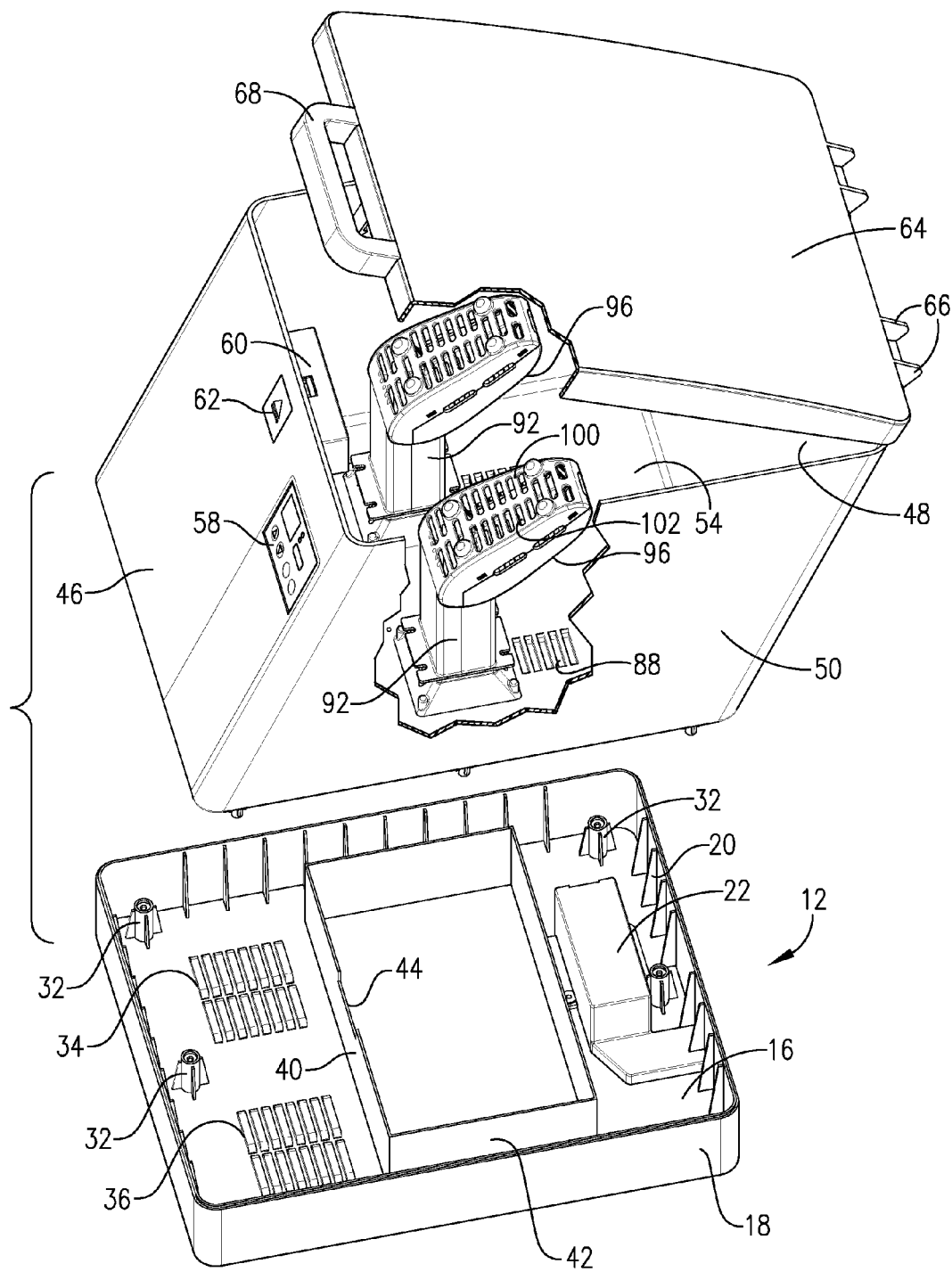
FIG. 5 is an exploded view with parts broken away illustrating components of the apparatus.

The underside of lower wall 54 has a series of depending tubular couplers 76 designed to rest upon and mate with the tubular coupling fixtures 32 of base 12 (see FIG. 3). Screws (not shown) extend upwardly through the fixtures 32 and into the couplers 76 to secure the housing 14 to base 12. In addition, the lower wall 54 has a rectangular wireway opening 78, which communicates with the interior of channel housing 63, and a pair of primary, side-by-side airflow conduits 80. Each conduit 80 includes upwardly extending and converging walls 82 defining a passageway opening 84. Two series of vent openings 86 and 88 are respectively located adjacent each conduit 80.

A pair of tubular, juxtaposed, generally L-shaped shoe trees 90 are provided within housing 14, with one tree mounted on each conduit 80. Each tree 90 includes an upright, tubular shank 92 having a lowermost flange 94, as well as an obliquely extending head 96. The shanks 92 are each preferably imperforate so as to ensure maximum air delivery to the heads 96. A series of connecters 98 are used to secure the flange 94 to the associated conduit 80. The head 96 has an upper wall or face 100 equipped with a series of openings 102 therein, as well as a bottom wall or face 104 also equipped with openings 106. Sidewalls 108 each extend between the upper and bottom faces 100, 104 and also have vent openings 110.

A pair of tubular mounts 112 extend from the underside of lower wall 54 and are in registry with the conduits 80. Each mount 112 supports an electrical resistance heater 114. A powered fan 116 is provided. The fan 116 is preferably in the form of a pair of blowers 117, each positioned on a respective mount 112. Threaded connectors (not shown) are employed to secure each blower 117 and mount 112 to the underside of lower wall 54, so that the bottom surface of each blower 117 is spaced above the lower wall 54 of housing 14.

An ozone generator 118 is secured to the underside of lower wall 54 generally between the mounts 112. The generator 118 may be any type of unit, such as a corona discharge or UV generator.

As indicated previously, the operation of apparatus 10 is controlled through the controller 58. The controller wiring extends downwardly through channel housing 63 and wireway opening 78, where it is operatively connected with electronic control boards (not shown) mounted on the connector bars 34, 36. Additional wiring is provided to the fan 116, heaters 114, and ozone generator 118 so as to govern the operation of the apparatus 10. It will be appreciated that the control circuitry for the apparatus 10 is itself conventional and typically would include a programmable microprocessor, such as a digital programmable logic controller (PLC).

Moreover, programming of such a device is within the skill of the art.

When it is desired to utilize apparatus 10 for deodorizing and sanitizing items such athletic shoes 120 (FIG. 3), the cover 64 is opened and the shoes 120 are mounted on the respective trees 90, so that the heads 96 thereof are inserted fully into the shoes 120. The lid 64 is then closed, and the controller 58 is activated to initiate the deodorizing/sanitizing operation. The controller 58 is preferably configured to initially actuate both the fan 116 and heater 114 so as to first dry the shoes 120. This causes ambient air to be drawn through the bottom vent openings 26, 28 and then through the relieved area 44 of sidewall 40. The air is then pulled upwardly through each blower 117, across the heater 114, and into the conduit 80 for ultimate passage through the respective tree 90. Such air then passes into the shoes 120 in order to dry them. Additional heated air also passes upwardly through the vents 86, 88 to dry the exterior surfaces of the shoes. The air currents developed in this fashion exit the zone 56 through the rear wall aperture 74. In one aspect of the invention, the aperture 74 is sized relative to the output of the fan 116 so as to maintain within the zone 56 a small positive pressure. This pressure facilitates rapid and effective drying of the shoes 120.

The heating step may be manually eliminated by pressing a "no heat" button (not shown) on the control panel, if desired. (The controller may also be configured to automatically eliminate the heating step, e.g., if the shoes are already dry. This may be sensed by a suitable humidity sensor within the zone 56.) Once any heating step is completed, the fan 116 remains on and the ozone generator 118 is actuated by the controller 58. This causes ambient air to be drawn through the bottom vent openings 26, 28 and then through the relieved area 44 of sidewall 40. This air swirls within the compartment 38 and ozone emitted by the generator 118 mixes with the air. The ozone-laden air is then pulled upwardly through each blower 117 and conduit 80 for ultimate passage through the respective tree 90. Such air then passes into the shoes 120 in order to deodorize and sanitize them. Additional ozone-laden air also passes upwardly through the vents 86, 88 to deodorize and sanitize the exterior surfaces of the shoes. The air currents developed in this fashion exit the zone 56 through the rear wall aperture 74. In one aspect of the invention, the aperture 74 is sized relative to the output of the fan 116 so as to maintain within the zone 56 a small positive pressure. This pressure facilitates the rapid and effective deodorizing and sanitizing of the shoes 120.

If desired, the heaters 114 may be energized again, during ozone treatment, or alternatively after ozone treatment.

In normal circumstances, the duty cycle for the apparatus 10 is on the order of one (1) to two (2) hours, but this of course depends upon the size and nature of the shoes 120. Normally, when a treatment cycle has terminated, the fan 116 is powered for an additional period, e.g., five (5) minutes, in order to clear the zone 56 of any contaminants and to assure that the apparatus 10 returns to ambient temperature.

Although the invention has been illustrated in the context of a purpose-built apparatus, it will be appreciated that the principles of the invention may be applicable to other types of containers, such as lockers or chests. Likewise, the specific configuration of the object holding structures within the apparatus can readily be modified to support different types of shoes, clothing, or equipment which require periodic deodorizing and sanitizing.

It has been found that placing the ozone generator 118 in a relatively small compartment, such as the compartment 38, augments the operability of the apparatus 10. That is, if the generator were placed within the large zone 56, it would take considerably longer to generate an effective concentration of ozone within the zone, than is the case with the invention. Placing the generator within the compartment allows a rapid buildup of ozone, which is delivered to the zone 56 without premature dissipation thereof. By the same token, passage of the ozone-laden air upwardly through the imperforate tubular shanks 92 assures that the relatively high ozone concentration in such air is only released through the perforate heads 96, which are within the athletic shoes 120. Furthermore, the combination of heating and ozone treatment and, more particularly, the preferred sequence of heating followed by ozone treatment, provides highly effective deodorizing and sanitizing of the shoes 120.

It will thus be seen that the apparatus of the invention provides a means for rapid and complete deodorizing and sanitizing of items such as shoes or other clothing. This treatment removes odors, kills odor-producing microorganisms, and, when the heaters 114 are employed, effectively dries the items being treated.

Although the above description presents features of preferred embodiments of the present invention, other preferred embodiments may also be created in keeping with the principles of the invention. Furthermore, these other preferred embodiments may in some instances be realized through a combination of features compatible for use together despite having been presented independently as part of separate embodiments in the above description.

The preferred forms of the invention described above are to be used as illustration only and should not be utilized in a limiting sense in interpreting the scope of the present invention. Obvious modifications to the exemplary embodiments, as hereinabove set forth, could be readily made by those skilled in the art without departing from the spirit of the present invention.

The inventors hereby states their intent to rely on the Doctrine of Equivalents to determine and assess the reasonably fair scope of the present invention as pertains to any apparatus not materially departing from but outside the literal scope of the invention set forth in the following claims.

What is claimed is:
1. Deodorizing and sanitizing apparatus, comprising:
structure defining an enclosed treatment zone operable to hold an item of clothing for treatment,
said zone-defining structure comprising a housing that includes a lower wall;
a base including a bottom wall, a sidewall, and an internal compartment,
said sidewall projecting upwardly from the bottom wall to generally present an outer lateral periphery of the base,
said compartment being defined by upright wall structure projecting from the bottom wall of the base,
said upright wall structure being spaced laterally inward from the sidewall, such that the internal compartment is spaced from the outer periphery of the base;
an ozone generator positioned below the lower wall within the compartment, such that the generator is outside the treatment zone and housed within the compartment; and
a ventilation assembly operable to create currents of air containing ozone from said generator, and to pass such ozone-laden air currents in proximity to said item for a period of time sufficient to deodorize and sanitize the item.

2. The apparatus of claim 1, said housing having an openable cover allowing access to the interior of the housing.

3. The apparatus of claim 1, said ventilation assembly comprising a fan operable to induce ambient air currents, and to direct such currents past said generator in order to create said ozone-laden air currents, said ozone generator being located proximal to said fan.

4. The apparatus of claim 3, said fan being located within the compartment separate from said zone, there being a passageway for delivery of said ozone-laden air from said compartment and into said zone.

5. The apparatus of claim 1, there being a shoe tree within said zone operable to support a shoe to be treated, said shoe tree comprising an upright, tubular shank, and a perforate head extending from said shank, said ventilation assembly operable to pass said ozone-laden air currents through said shank and head to deliver the ozone-laden air into the confines of said shoe.

6. The apparatus of claim 5, said housing having an openable cover allowing access to the interior of the housing, said shoe tree being within the interior of the housing.

7. The apparatus of claim 6, including a heater located in the path of said air currents in order to heat the air currents.

8. The apparatus of claim 1, including a heater located in the path of said air currents in order to heat the air currents.

9. The apparatus of claim 1, there being a vent opening formed in said zone-defining structure, said vent opening correlated with said ventilation assembly for creating a positive pressure within said zone during treatment of said item.

10. The apparatus of claim 1, including a controller operable to control the ventilation assembly and ozone generator, said controller being operable to simultaneously run the ventilation assembly and ozone generator simultaneously.

11. The apparatus of claim 10, including a heater located in the path of said air currents in order to heat the air currents, said controller being operable to control the heater, said controller being operable to simultaneously run the ventilation assembly and heater.

12. The apparatus of claim 11, said controller being operable to run the heater and the ozone generator in sequence.

13. The apparatus of claim 1, said wall structure extending into flush contact with the lower wall of the housing except for a vent relief defined in the wall structure.

14. Deodorizing and sanitizing apparatus for shoes, comprising:
a base including a bottom wall, an upstanding side wall, and an internal compartment spaced at least in part from the sidewall;
a housing defining a shoe treatment zone secured to said base and extending upwardly therefrom, said housing having a lower wall, upright outer walls, and an openable cover;
a pair of upright shoe trees secured to said housing lower wall and extending upwardly therefrom, said trees each comprising a tubular, imperforate shank and a perforate head extending laterally from the shank, said shoe trees operable to support a pair of shoes to be treated, with said heads being configured for placement within the confines of the shoes;
an ozone generator positioned within said internal compartment and below said housing lower wall, such that the generator is outside the zone; and
a ventilation assembly operable to create currents of air containing ozone from said generator, and to pass such ozone-laden air currents through said shoe tree shanks and said heads in order to deodorize and sanitize the shoes,
said ventilation assembly including a fan and a conduit operably coupled with each of said shanks and communicating the interiors of the shanks with the fan,
said conduit extending upwardly from the lower wall and being operably coupled with each of said shanks,
said ventilation assembly further including a tubular mount extending downwardly from the lower wall in registry with the conduit,
said ventilation assembly further including a heating element being supported within the tubular mount,
said fan being operably coupled to the tubular mount beneath the heating element, such that the fan is operable to force ozone-laden air across the heating element, through the conduit, and into the interior of each shank.

15. The apparatus of claim 14, said fan located within the compartment of said base.

16. The apparatus of claim 14, including a pair of said heating elements each being located within a corresponding one of said conduits for heating of said air currents.

17. The apparatus of claim 14, said shoe tree heads comprising top and bottom faces each having air passageways formed therein.

18. The apparatus of claim 14, said base bottom wall having air inlet vents, said ventilation assembly operable to draw ambient air currents through said air inlet vents and into adjacency with said ozone generator.

19. The apparatus of claim 14, said fan including a pair of blowers, each being associated with a respective one of the shanks.

20. The apparatus of claim 19, said ozone generator being located generally between the blowers.

21. The apparatus of claim 14, including a controller operable to control the ventilation assembly and ozone generator, said controller being operable to simultaneously run the ventilation assembly and ozone generator simultaneously.

22. The apparatus of claim 21, said controller being operable to control the heating element, said controller being operable to simultaneously run the ventilation assembly and heating element.

23. The apparatus of claim 22, said controller being operable to run the heating element and the ozone generator in sequence.

24. The apparatus of claim 14, said compartment defined by upright wall structure, said upright wall structure being spaced entirely from the sidewall.

25. The apparatus of claim 14, said compartment defined by upright wall structure, said upright wall structure being spaced entirely from the sidewall, said upright wall structure projecting from the bottom wall of the base.

26. The apparatus of claims 25, said wall structure extending into flush contact with the lower wall of the housing except for a vent relief defined in the wall structure.

* * * * *